(12) United States Patent
Worthington (10) Patent No.: US 8,454,363 B2
(45) Date of Patent: Jun. 4, 2013

(54) DENTAL IMPLANT SYSTEM

(76) Inventor: William B. Worthington, Louisville, KY (US)

( * ) Notice: Subject to any disclaimer, the term of this patent is extended or adjusted under 35 U.S.C. 154(b) by 0 days.

(21) Appl. No.: 12/461,954

(22) Filed: Aug. 28, 2009

(65) Prior Publication Data

US 2010/0112520 A1 May 6, 2010

Related U.S. Application Data

(60) Provisional application No. 61/111,941, filed on Nov. 6, 2008, provisional application No. 61/215,954, filed on May 12, 2009.

(51) Int. Cl.
*A61C 8/00* (2006.01)
(52) U.S. Cl.
USPC ......................................................... 433/174
(58) Field of Classification Search
USPC .................................................. 433/172–176
See application file for complete search history.

(56) References Cited

U.S. PATENT DOCUMENTS

| | | | |
|---|---|---|---|
| 3,979,828 A | 9/1976 | Taylor | |
| 4,215,986 A | 8/1980 | Riess | |
| 4,216,548 A | 8/1980 | Kraus | |
| 4,318,696 A * | 3/1982 | Kasama et al. | 433/173 |
| 4,416,629 A | 11/1983 | Mozsary et al. | |
| 4,540,367 A * | 9/1985 | Sulc | 433/181 |
| 4,722,688 A | 2/1988 | Lonca | |
| 5,026,280 A | 6/1991 | Dürr et al. | |
| 5,061,181 A | 10/1991 | Niznick | |
| 5,087,201 A | 2/1992 | Mondani et al. | |
| 5,098,294 A | 3/1992 | Lee et al. | |
| 5,098,295 A | 3/1992 | Dürr et al. | |
| 5,211,561 A | 5/1993 | Graub | |
| 5,368,483 A | 11/1994 | Sutter et al. | |
| 5,376,004 A | 12/1994 | Mena | |
| 5,468,150 A | 11/1995 | Brammann | |
| 5,554,027 A | 9/1996 | Brånemark | |
| 5,556,280 A * | 9/1996 | Pelak | 433/172 |
| 5,564,924 A | 10/1996 | Kwan | |
| 5,588,838 A | 12/1996 | Hansson et al. | |
| 5,620,323 A | 4/1997 | Bressman et al. | |
| 5,749,732 A | 5/1998 | Sendax | |

(Continued)

FOREIGN PATENT DOCUMENTS

WO WO 2004/108014 12/2004

OTHER PUBLICATIONS

Website, http://www.bicon.com/tech/t_iac01.html, description of Bicon Integrated Abutment Crown and method of forming a dental impression, two sheets printed from the internet on Jan. 11, 2009.

*Primary Examiner* — Sunil K Singh
(74) *Attorney, Agent, or Firm* — Richard C. Litman (57) ABSTRACT

The dental implant system includes implants having integral abutments therewith for the removable or fixed attachment of plural or single prosthetic teeth, as appropriate. The system for removable dental prostheses includes a metal housing permanently installed in the removable prosthesis, and a rubber retentive insert installed in the housing. The insert is removably installed over the abutment of the implant to secure the dental prosthesis thereto. The system includes transfer copings for transferring an impression to the lab for manufacture of the prosthesis, and lab processing copings and analogs for handling and forming the prosthesis during manufacture. The system may be assembled as a kit having some or all of the above components.

12 Claims, 8 Drawing Sheets

U.S. PATENT DOCUMENTS

| | | |
|---|---|---|
| 5,759,034 A | 6/1998 | Daftary |
| 5,967,783 A | 10/1999 | Ura |
| 6,039,568 A | 3/2000 | Hinds |
| 6,099,312 A | 8/2000 | Alvaro |
| 6,227,856 B1 | 5/2001 | Beaty et al. |
| 6,305,939 B1 | 10/2001 | Dawood |
| 6,394,808 B2 | 5/2002 | Rizzo et al. |
| 6,461,160 B1 | 10/2002 | Sutter |
| 6,547,564 B1 | 4/2003 | Hansson |
| 6,709,270 B2 | 3/2004 | Honkura et al. |
| 6,716,030 B1 | 4/2004 | Bulard et al. |
| 6,923,648 B1 * | 8/2005 | Rassoli ................. 433/173 |
| 6,951,460 B2 | 10/2005 | Halldin et al. |
| 6,997,711 B2 | 2/2006 | Miller |
| 7,018,207 B2 | 3/2006 | Prestipino |
| 7,033,174 B2 | 4/2006 | Giorno |
| 7,066,736 B2 | 6/2006 | Kumar et al. |
| 7,179,089 B2 | 2/2007 | Sims et al. |
| 7,264,470 B2 | 9/2007 | Hansson |
| 7,270,542 B2 | 9/2007 | Cottrell |
| 7,300,282 B2 | 11/2007 | Sapian |
| 7,300,284 B2 | 11/2007 | Linder |
| 7,341,454 B2 | 3/2008 | Balfour et al. |
| 2002/0177103 A1 | 11/2002 | Pelak |
| 2003/0228556 A1 | 12/2003 | Giorno |
| 2003/0232309 A1 | 12/2003 | Dinkelacker |
| 2004/0018471 A1 | 1/2004 | Giorno |
| 2005/0214714 A1 | 9/2005 | Wohrle |
| 2007/0015110 A1 | 1/2007 | Zhang et al. |
| 2008/0050691 A1 | 2/2008 | Baughman et al. |
| 2008/0153063 A1 | 6/2008 | Mullaly et al. |
| 2009/0263763 A1 * | 10/2009 | Shepard ................. 433/174 |
| 2010/0009316 A1 * | 1/2010 | Hurson ................. 433/173 |

\* cited by examiner

DENTAL IMPLANT SYSTEM

CROSS-REFERENCE TO RELATED APPLICATIONS

This application claims the benefit of U.S. Provisional Patent Applications Ser. No. 61/111,941, filed on Nov. 6, 2008, and Ser. No. 61/215,954 filed on May 12, 2009.

BACKGROUND OF THE INVENTION

1. Field of the Invention

The present invention relates generally to the field of dentistry, and particularly to a dental implant system for mini dental implants.

2. Description of the Related Art

Traditional removable partial dentures, i.e., the replacement of a relatively few missing teeth with prosthetic teeth, have been secured in the mouth by means of relatively rigid wire or other metal attachments extending from the dentures and removably attached to adjacent teeth. Removable full dentures, which replace all or nearly all of the mandibular or maxillary teeth, have traditionally been adhesively secured in the mouth. Single prosthetic teeth, i.e., crowns, traditionally require at least some portion of the natural tooth for fixed attachment thereto.

More recently, various implants have been developed that anchor directly into the mandibular or maxillary bone structure, with the prosthetic tooth or teeth being permanently or removably attached to the protruding abutment of the implant. Most such implants are relatively large and are not suitable for-the medically, financially, or anatomically compromised patient. The installation of such larger implants is a multi-step procedure, with the patient initially receiving oral surgery to open the gingival tissue and expose the underlying bone structure, whereupon the bone is drilled and tapped for the implant and the implant is installed. The patient must then wait for the soft tissue to heal and for a considerable period of time for the bone to grow around the implant and anchor the implant firmly in place. A subsequent visit is required after healing for the dentist to make an impression of the area in which the dental prosthesis is to be installed. The impression is then sent out to a dental laboratory for the manufacture of the dental prosthesis. Finally, the completed prosthetic tooth or other dental prosthesis is fit into place during still another visit to the dentist.

Even more recently, so-called "mini-implants" or mini dental implants have been developed. These relatively small implants do not require specific lying open of the gingival tissue or the drilling of relatively large holes in the bone structure. Rather, the small hole for the miniature implant can be drilled directly through the gingival tissue and into the underlying bone. The mini-implant can be placed or installed in most all compromised patients. This is a minimally invasive approach and even the medically compromised patient, and particularly the edentulous patient, can withstand the placement procedure due to the stability of the mini-implant and prosthesis. In cases where the procedure is for the reinstallation of a retrofit denture or prosthesis, the mini-implant(s) can be installed and the prosthesis installed thereon in a single visit to the dentist. In the case of a new denture, the mini-implant(s) are placed during one visit, and the impression for the prosthetic tooth or teeth is made during the same visit. The patient returns in only a few days later for the final fitting of the new prosthesis after it has been manufactured in the dental laboratory. As can be seen, the use of mini-implants greatly reduces the time and effort, and thus the cost, of implant placement, as well as greatly reducing the trauma to the patient.

However, many if not most such implants are of multiple piece construction, with a threaded implant portion having an upper end fitting generally flush with the exposed gingival surface and an abutment portion that attaches to the implant in some manner. Moreover, it has been recognized that some cushioning is desired between the removable dental prosthesis and the underlying abutment, implant, and bone structure, thus relieving the stress otherwise imposed upon the implant. This has been accomplished in the past by means of a small O-ring installed between the dental prosthesis and the abutment, which has proven to be less than satisfactory. In practice, these systems tend to collect food residue between the retainer cap and the spherical head of the abutment, thus preventing the ball of the abutment from seating completely and resulting in an unstable and poorly fitting dental prosthesis.

Another problem that can occur in the placement of conventional miniature implants is that the impression material if not contained may flow into the crevice between the gum line and the overlying structure. This can result in some chance that the impression material (or prosthesis material, in the case of a retrofit installation) may be locked around the abutment and its retentive mechanism, within the overlying interface between the gingival surface and the overlying protruding abutment.

Thus, a dental implant system solving the aforementioned problems is desired.

SUMMARY OF THE INVENTION

The dental implant system comprises implants with integral abutments for use in securing both removable and fixed dental prostheses in the mouth. The system also includes components installed in the removable or fixed prostheses for securing the prostheses to the abutments of the implants. Various components are also provided for the formation of the prostheses and for their installation. Some or all of the various components of the present system may be combined as a kit, if so desired. A ratchet type instrument or tool having a drive socket may be provided for driving the implants, with the specific drive being configured as required for various abutment forms. Separate interfacing components having corresponding fittings for mating to the abutment of the implant and the socket of the instrument may also be provided.

In one embodiment, the system comprises a threaded mini-implant having an integral abutment. A metal retentive housing includes a rubber retentive insert removably installed therein. The metal housing is permanently affixed in the dental prosthesis. The rubber insert installs removably over the abutment of the implant to permit the dental prosthesis to be removed and reinstalled as desired. A rubber gasket or ring is provided at the time of forming the impression or retrofitting an existing dental prosthesis. The gasket or ring is placed about the base of the abutment to prevent the flow of impression material into the gap between the gingival tissue and the overlying prosthetic retainer.

Another embodiment comprises a mini-implant with an asymmetric abutment that generally simulates the contours of a natural tooth. This implant is used for the installation of a fixed dental prosthesis, e.g., a single artificial tooth, or perhaps a plurality of implants for several teeth.

Yet another embodiment includes a transfer coping installed on the abutment at the time of forming the impression. The transfer coping is captured and becomes an integral component of the impression so that an analog may be placed for making a model of the structure.

Another embodiment includes a laboratory (lab) processing coping, with the lab processing coping serving two functions. First, the dentist can try the coping at the time of placement of the dental mini implant to assure that the finish line, i.e., the boundary between the base of the abutment structure and the overlying dental prosthesis, is sub-gingival in order to provide a seal between the prosthetic structure and the surrounding tissue to preclude the entry of food residue therein. Secondly, the laboratory technician can use the lab processing coping to fabricate the prosthetic material in the construction of the fixed prosthesis. An analog and sleeve assembly is also provided for handling the impression and for forming the dental prosthesis from the impression.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The present invention relates to a dental implant system incorporating mini dental implants having abutments formed integrally therewith. The system includes implant embodiments for installing both removable and fixed dental prostheses, as well as components for use with transfer and lab processing copings and an analog and pin with a locking feature for use during the manufacture of the prosthesis. The various components of each embodiment may be provided as a kit, if so desired.

Figure 1:
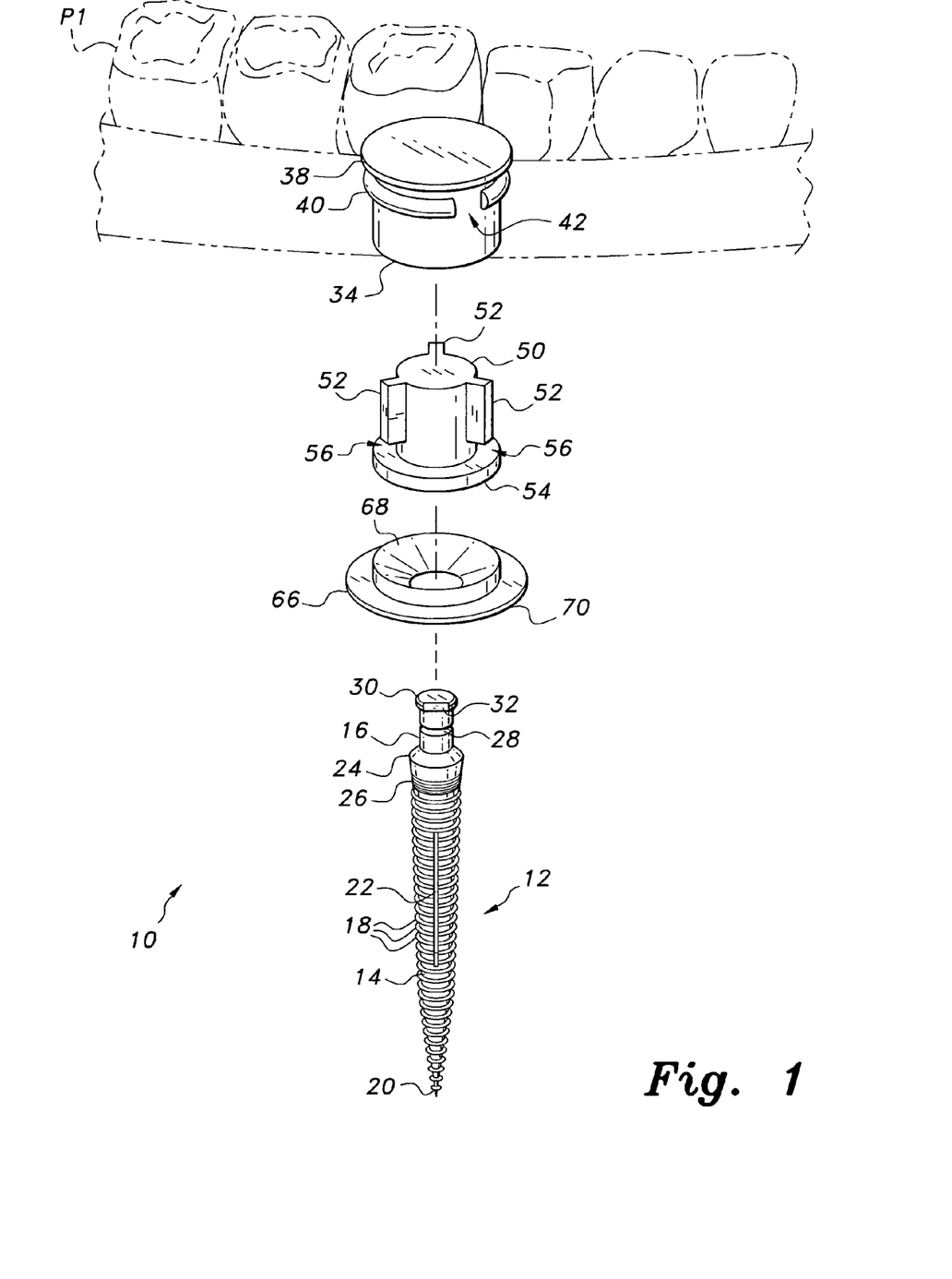
FIG. 1 is an exploded perspective view of a dental implant and prosthetic attachment assembly in a dental implant system according to the present invention, showing its various components.
Figure 2:
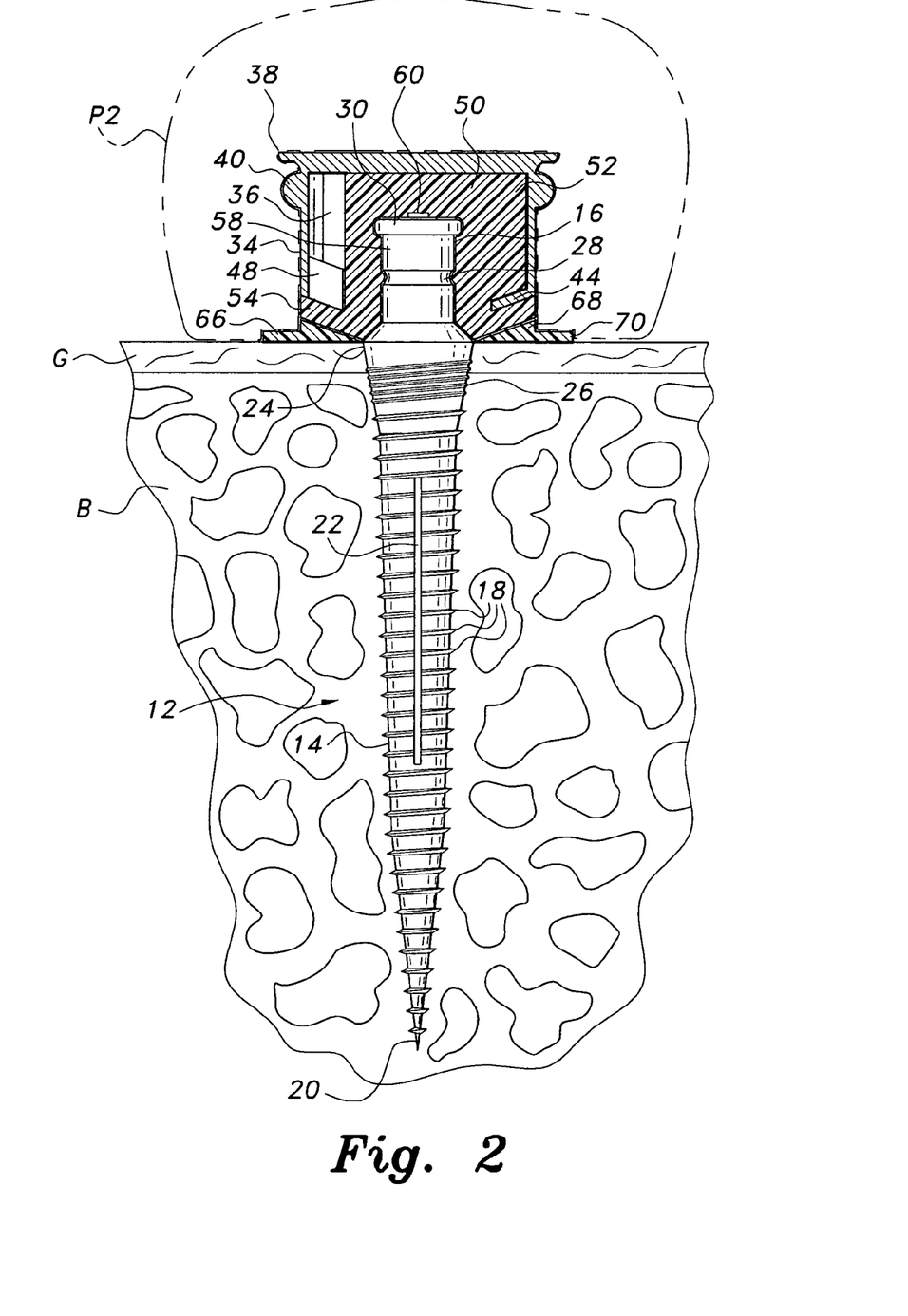
FIG. 2 is an elevation view in section of the installed implant and prosthetic attachment assembly of FIG. 1, illustrating further details.
Figure 3:
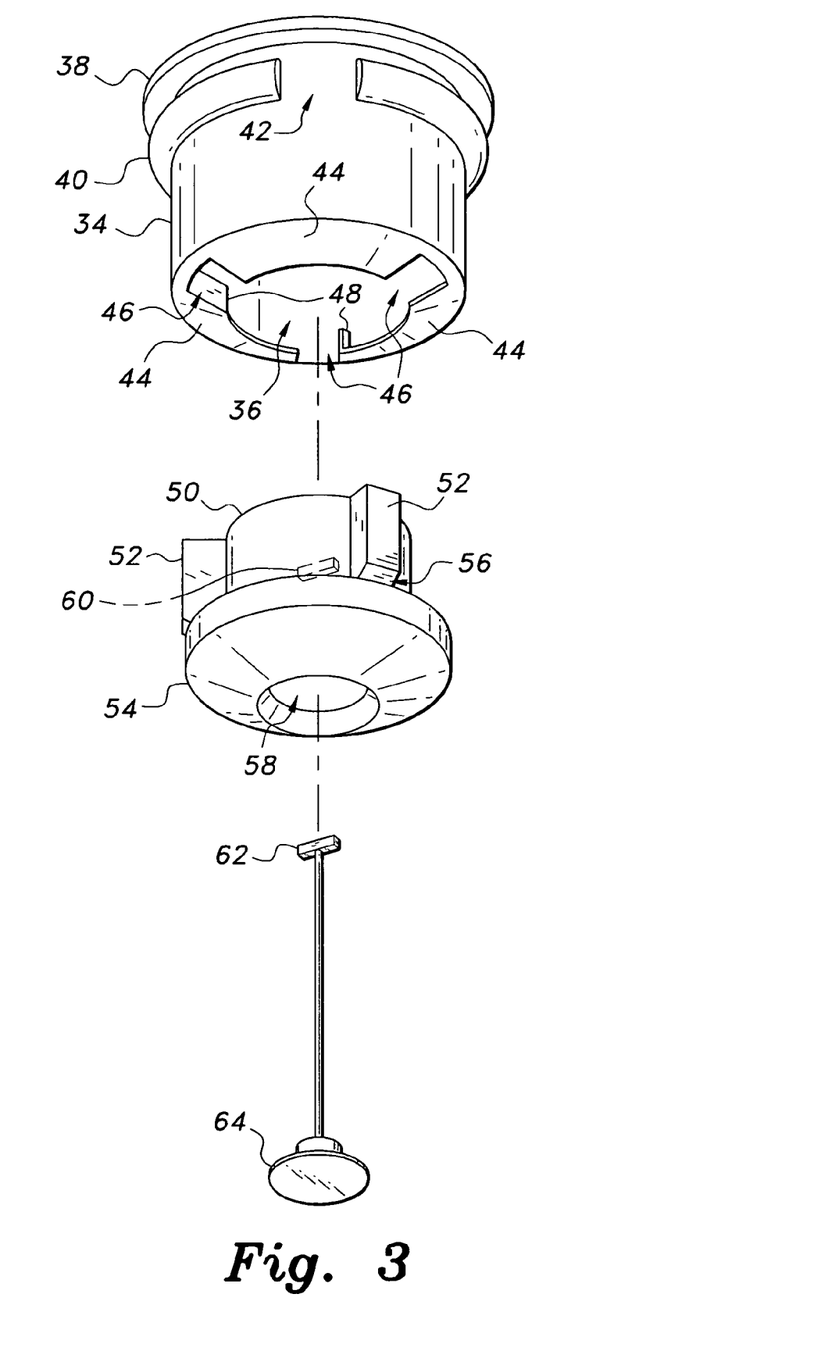
FIG. 3 is an exploded perspective view of a metal retentive housing and rubber retentive insert in a dental implant system according to the present invention, shown with an instrument used for their assembly.

FIGS. 1 through 3 of the drawings illustrate the components and exemplary installation of a first embodiment of the dental implant system, comprising an assembly wherein the dental prosthesis is removably secured within the mouth of the user. FIG. 1 of the drawings provides a perspective view of a kit 10 for the installation of a removable prosthesis in the mouth, with FIG. 2 providing an elevation view in section of the completed installation and FIG. 3 illustrating the assembly of certain components of the system.

The assembly and installation shown in FIGS. 1 through 3 uses a miniature dental implant 12. The implant 12 is a so-called "mini" implant, i.e., having a total length, including the threaded base portion 14 and abutment portion 16, of about 16 to 23 mm, more or less, with the base 14 and abutment 16 being formed as a single integral component. The base 14 includes helical threads 18 thereon, and tapers to a pointed distal tip 20. The helically threaded base 14 further includes one or more axial grooves 22 therein, with the grooves 22 serving to accept bone growth during the healing process to prevent the implant 12 from rotating within the bone structure and to provide greater anchorage and security for the implant 12. The threaded base portion 14 is narrow in width, having a diameter of about 2.4 mm, or between about 1.8 mm and 2.9 mm.

The opposite end of the base portion 14 includes a sub-gingival collar 24 having a conical taper to the helical threads 18 of the base portion 14, with the conical taper having a smooth and unthreaded upper portion with a plurality of very fine "micro-threads" 26 extending about the lower portion to the helical threads 18 of the base portion 14. The relatively finely cut micro-threads 26 provide a better seal between the implant 12 and the surrounding bone or tissue structure once the implant has been installed. As the name implies, the conical sub-gingival collar 24 extends somewhat below the gingival tissue G and into the underlying bone structure B so that the micro-threads 26 engage the outermost cortical bone material, generally as shown in FIG. 2 of the drawings. The top or widest diameter portion of this sub-gingival collar 24 is described as a "finish line," and resides essentially level with the upper surface of the soft gingival tissue in the removable denture embodiment of FIGS. 1 and 2.

The abutment 16 has an essentially cylindrical shape and a circumferential groove 28 formed thereraround. This groove 28 serves as a seating element and anchor for a resilient elastomeric (rubber, etc.) insert that is removably installed over the abutment 16, as explained further below. The abutment 16 has a head 30 opposite the sub-gingival collar 24. The head 30 has a somewhat larger diameter than that of the balance of the abutment 16. The head 30 is of a non-circular configuration, e.g., it includes at least one flat 32 or other non-circular element (e.g., a notch, etc.) formed in the periphery thereof, as shown in FIG. 1. This provides for the placement of a torsion instrument or adapter over the head 30 of the abutment 16 for turning the implant 12 and advancing it into a hole previously formed in the bone structure. The relatively small diameter and length of the helically threaded base portion 14 of the implant 12 allows it to be screwed into a previously formed unthreaded hole without the need to perform the extra step of threading the hole. The self-tapping helical threads 18 enhance the physical security of the implant installation.

A prosthesis-retaining housing 34 is permanently affixed (i.e., cast or molded in place) within the dental prosthesis P. In the example of FIG. 1, the dental prosthesis P1 is shown in broken lines as a section or portion of a removable partial or full denture or the like. The housing 34 is embedded in the lower portion or tissue side (internal surface) of the prosthesis P1. While a full or partial denture would be the most common installation for a removable prosthesis in the dental implant system, it will be seen that the same configuration may be applied to smaller, individual tooth prostheses, e.g., the single tooth prosthesis P2 of FIG. 2, if so desired.

The housing 34 is preferably formed of thin metal, and has a generally cylindrical configuration with a closed top or cap defining a hollow interior 36 (shown in FIGS. 2 and 3). The top or cap includes an outwardly extending circumferential flange 38, serving to prevent the housing 34 from pulling out of the dental prosthesis P1. An outwardly protruding circumferential bead or band 40 extends about the housing 34, the band 40 including at least one break or discontinuity 42 therein. This break or discontinuity 42 provides for the inclusion of material of the removable dental prosthesis P1 to flow therein during manufacture of the prosthesis, thus precluding rotation of the otherwise circular or cylindrical retaining housing 34 within the prosthesis P1.

Further details of the retaining housing 34 are shown in FIGS. 2 and 3. FIG. 3 particularly illustrates the means for retaining the elastomeric insert therein. The lower edge or base of the generally cylindrical housing 34 includes an inwardly extending base flange 44 defining a shallow conical shape. The flange 44 serves to retain the insert therein. The flange 44 includes a plurality of radially disposed slots 46 defined therein to permit the insertion of the insert into the housing 34, with each slot 46 having a stop tab 48 formed from the upwardly bent end of the adjacent flange portion.

The resilient elastomeric insert 50 serves as a connecting element between the housing 34, which is permanently affixed into the prosthesis P1 or P2, and the abutment portion 16 of the implant 12, which is permanently installed in the mandibular or maxillary bone structure of the patient. The insert 50 is of a generally cylindrical configuration. The diameter of the insert 50 closely matches the diameter of the passage defined by the base flange 44 of the retaining housing 34. The insert 50 has a series of axial ribs 52 extending radially from the cylindrical core. The ribs 52 are aligned with and closely fit through the slots 46 of the base flange 44 of the housing 34 when the insert 50 is installed therein. The diameter defined by the outer reaches of the ribs 52 closely matches the internal diameter of the housing 34, to provide a closer fit between the insert 50 and housing 34 when the insert 50 is installed therein.

The insert 50 has a cushioning flange 54 extending radially from and circumferentially about the base of the insert 50. The cushioning flange 54 fits below the base flange 44 of the housing when the insert 50 is installed therein. The lower ends of the axial ribs 52 and the cushioning flange 54 define gaps 56 therebetween, to allow the base flange 44 of the housing 34 to fit between the ribs 52 and cushioning flange 54 of the insert 50. The cushioning flange 54 serves as a cushion or shock absorber between the metal retentive housing 34 and the shoulder of the abutment 16 for the removable prosthesis P1 of FIG. 1 or the single tooth P2 of FIG. 2, and the oral structure of the patient when the assembly is completed and installed in the mouth of the patient.

The resilient elastomeric insert 50 has an abutment receptacle 58 formed concentrically therein. The receptacle 58 provides for the removable installation of the insert 50 (and attached housing 34 and dental prosthesis P1 or P2) to the abutment 16 of the implant 12. The receptacle 58 is configured to closely fit the contours of the abutment 16, i.e., having an inwardly formed circumferential rib to fit the abutment groove 28, a circumferential groove formed in the head of the receptacle 58 to fit the corresponding circumferential flange of the head 30 of the abutment 16, and an inward conical taper at the mouth of the receptacle 58 to fit the conical collar 24 or shoulder of the abutment 16.

The insert 50 is installed within the housing 34 by aligning the ribs 52 of the insert 50 with the slots 46 in the base flange 44 of the housing 34, and inserting the insert 50 axially into the housing 34. The insert 50 is then locked into the housing 34 by twisting or rotating the insert 50 within the housing 34 until the ribs 52 are stopped by the stop tabs 48 at one edge of each of the slots 46. This captures the ribs 52 of the insert 50 above the base flange 44 of the housing 34 to prevent the insert 50 from pulling out of the housing 34. The rotation of the insert 50 in the housing 34 also closes or covers the slots 46 of the housing 34, thereby precluding entrance of foreign matter into the housing.

The abutment receptacle 58 of the insert 50 includes a non-circular instrument receptacle 60 in the upper end thereof, i.e., opposite the opening through the cushioning flange 54. This instrument receptacle 60 allows the similarly shaped bit 62 of an insert installation instrument 64 to be inserted therein. Rotation of the instrument 64 produces corresponding rotation of the insert 50 within the housing 34. Removal of the insert 50 from the housing 34 is accomplished by rotating the instrument 64, and thus the insert 50, in the opposite direction from that used to lock the insert 50 in place within the housing 34, and withdrawing the insert 50 axially from the housing 34. The process requires but a few minutes to remove and replace worn inserts 50 in a removable partial or full dental prosthesis P1, and is easily accomplished in the dental office, or even at home by the owner of the dental prosthesis.

Dental prostheses are conventionally formed by molding a pliable or semi-liquid material (plastic, etc.) in the mouth of the patient in order to provide a close and precise fit between the oral structure of the patient and the dental prosthesis. The insert 50 and housing 34 are installed on the previously installed implant 12, and the material flows or is molded about the housing 34 to become an integral part of the removable prosthesis, or for a retrofit, an existing removable prosthesis. It will be seen that the semi-liquid characteristics of the material used to form the model will allow this material to flow beneath the conical cushioning flange 54 of the insert 50.

Accordingly, an elastomeric ring 66 is provided to serve as a seal between the cushioning flange 54 of the insert 50 and the underlying oral structure of the patient during the process of making an impression for a new prosthesis or retrofitting an existing prosthesis. The elastomeric ring 66 includes a central passage therein to fit about the abutment 16 of the insert 12, and a conically sloped intermediate portion 68 extending outwardly therefrom to a thin, flat outer sealing flange 70. The intermediate portion 68 closely fits the conical shape of the bottom of the cushioning flange 54 of the insert 50, and precludes the introduction of material between the flange 54 and the underlying soft tissue (gum) during the formation of the impression for the prosthesis. Once the impression has been formed and removed from the mouth of the patient (along with the housing 34 and insert 50 captured therein), the elastomeric ring 66 is removed from the abutment 16 and discarded.

Figure 4:
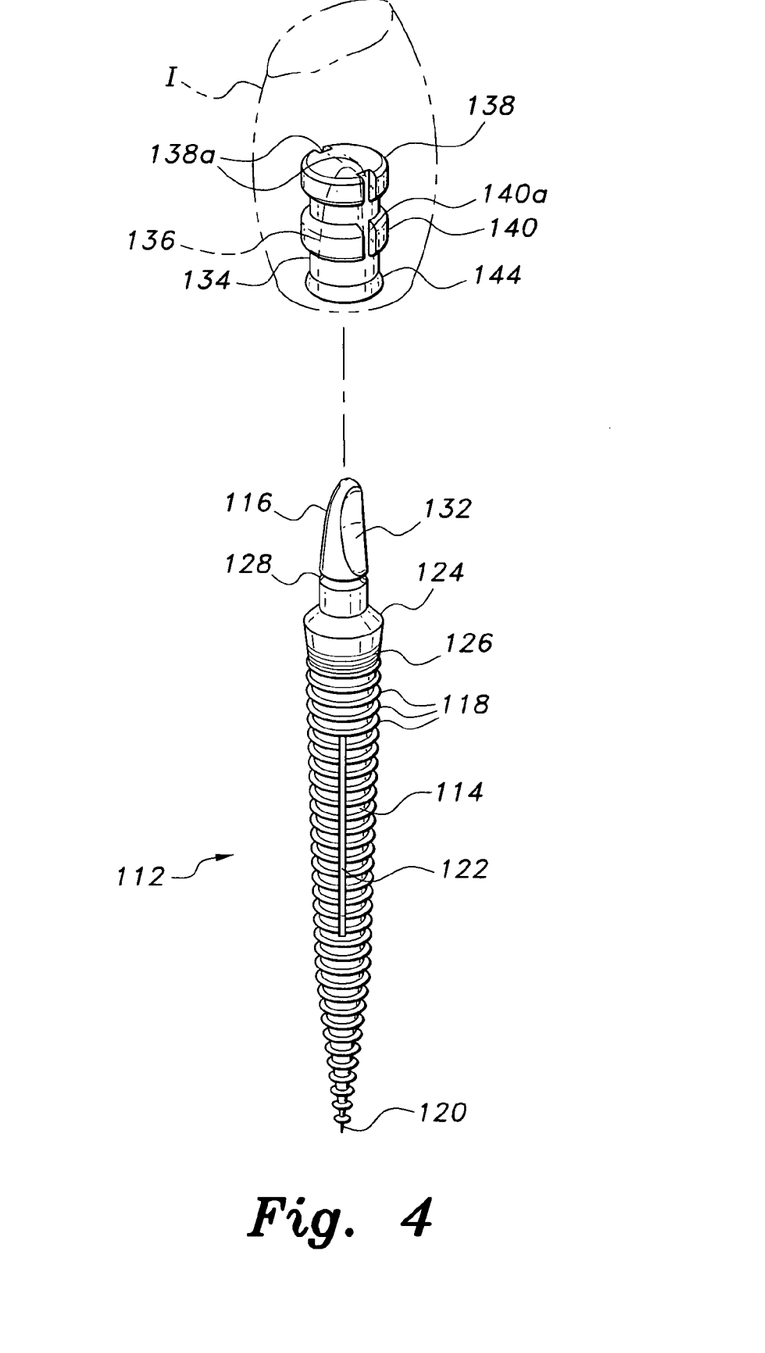
FIG. 4 is an exploded perspective view of an implant adapted for the attachment of a fixed dental prosthesis thereon, and the transfer coping for forming the prosthesis on the abutment of the implant, in a dental implant system according to the present invention.
Figure 6:
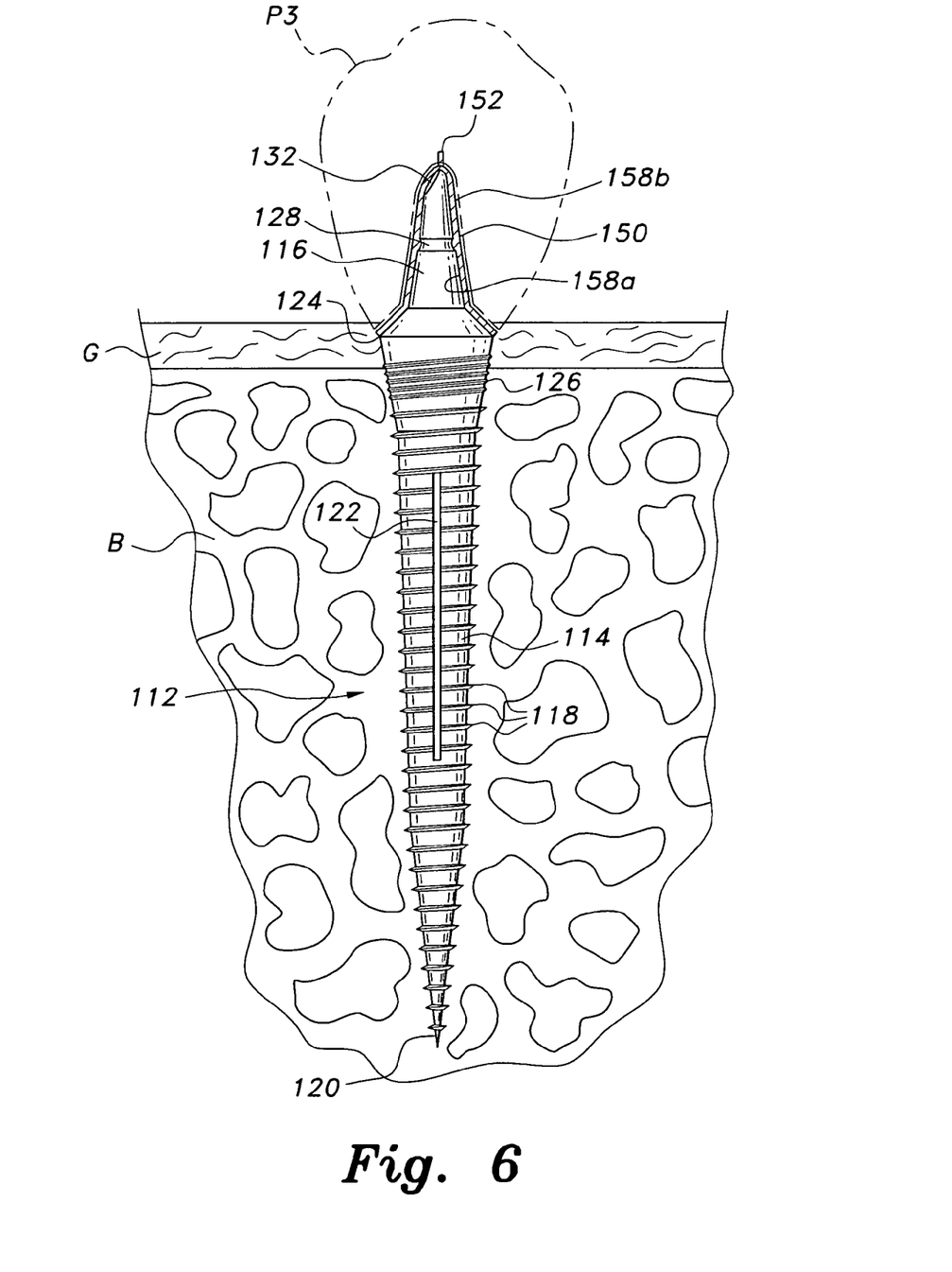
FIG. 6 is an elevation view in section of an installed implant and a lab processing coping used in the fabrication of a fixed dental prosthesis in a dental implant system according to the present invention.

FIGS. 4 through 6 illustrate components used in the manufacture and installation of one embodiment of a fixed dental prosthesis. These components may be provided as a group in the form of a kit, if so desired. The implant 112 of FIGS. 4 and 6 is similar to the implant 12 of FIGS. 1 and 2, and is in fact identical thereto from the finish line, i.e., the widest diameter or upper end of the sub-gingival collar 124 down, having a base 114 with helical threads 118 thereon and micro-threads 126 about the lower portion of the conical sub-gingival collar 124, a sharply pointed distal tip 120, and one or more axial grooves 122 formed along the base 114.

The abutment portion 116 of the implant 112 has a significantly different configuration from the corresponding abutment 16 of the implant 12 of FIGS. 1 and 2, however. The abutment 116 is shaped or configured to conform to the interior shape and configuration of both the transfer coping 134 shown in FIG. 4, and the lab processing coping illustrated in FIGS. 5 and 6. The abutment 116 has a generally smoothly curved or rounded upper or distal portion, with a circumferential groove 128 formed therein at about one third of the distance from the base to the tip of the abutment 116. A labial or forwardly oriented flat 132 is provided for abutments and implants configured for use with frontal (anterior) tooth prostheses.

The transfer coping 134 includes an abutment receptacle 136 defined therein that is configured to fit closely about the abutment 116. The transfer coping 134 has a generally cylindrical external shape and an outwardly extending circumferential flange 138 at the top of the coping 134, and an outwardly protruding circumferential band 140 extending about the coping 134. The flange 138 and/or band 140 are preferably non-circular, i.e., having a flat or other non-circular discontinuity formed thereon or therein in the manner of the flat 32 formed along the side or edge of the head 30 of the abutment 16 of FIG. 1. A discontinuity or gap, respectively 138a and 140a for the flange 138 and band 140, may be provided to serve this function. This prevents the impression I (shown in broken lines in FIG. 4) from rotating thereon, or the uninstalled coping 134 from rotating within the impression I. An outwardly extending or flaring skirt or flange 144 extends circumferentially about the base of the transfer coping 134 from the "finish line," i.e., the juncture between the base of the cylindrical body of the coping 134 and the skirt or flange 144. This skirt or flange 144 serves to expand and hold back the gingival tissue during the fitting of the transfer coping 134, in a manner similar to the use of packing cord about a natural tooth that has been prepared for a fixed prosthetic restoration.

Figure 5:
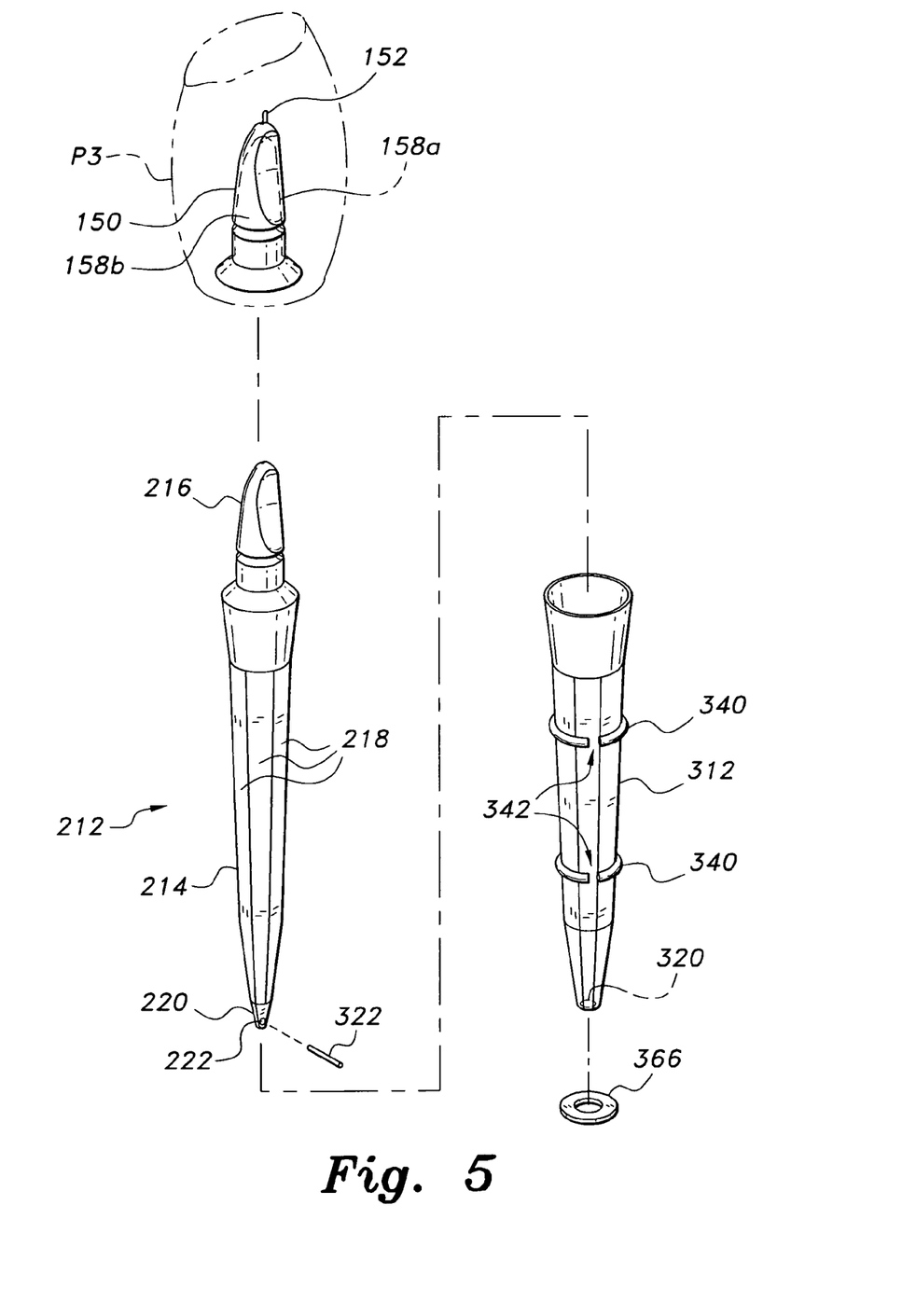
FIG. 5 is an exploded perspective view of an analog and pin and a sleeve used in the formation of a dental stone model and for receiving the lab processing coping in a dental implant system according to the present invention.

The process of forming and installing a single, fixed prosthetic tooth, e.g., the prosthetic tooth P3 of FIGS. 5 and 6, begins with the installation of the implant 112 into the jawbone structure of the patient, generally as described above for the removably installed dental prosthesis illustrated in FIGS. 1 through 3. A "stone model," i.e., a casting formed of material that cures into a hard and rigid structure, is formed of the patient's mouth, or more precisely, the stone model is formed to provide an analog of that portion of the patient's mouth in which the dental prosthesis is to be installed. The transfer coping 134 is placed upon the abutment 116 of the implant 112, and an impression I is formed over the transfer coping 134. Once the impression I has been formed, the impression I and the transfer coping 134 are removed together from the implant abutment 116. The transfer coping 134 and impression assembly is placed upon an implant analog pin in the stone model in order to send the impression I to a dental lab for manufacture of the fixed dental prosthesis, e.g., the prosthesis P3 of FIGS. 5 and 6.

An implant analog and pin 212 and associated components are illustrated in FIG. 5 of the drawings. The analog and pin 212 includes a base or pin portion 214 and an abutment or analog portion 216 extending upwardly therefrom. The pin or base 214 is devoid of threads, as it is not intended to be installed permanently in the stone model (or any other structure, as a permanent installation). However, it does have a non-circular cross section, e.g., longitudinal facets 218, in order to prevent it from rotating within a fixture or sleeve previously installed in the stone model during the manufacture of the prosthetic tooth. The abutment or analog portion 216 is configured to match precisely the internal contour and shape of the transfer coping 134 and also the lab processing coping 150 shown in FIGS. 5 and 6, which internally match precisely the external contours of the abutment of the implant previously affixed in the patient's mouth.

When the lab receives the assembly that includes the impression I and transfer coping 134 (FIG. 4) temporarily installed on the analog and pin 212 (FIG. 5), the base portion 214 of the analog pin is installed in a holder or sheath 312 (FIG. 5) in the stone model. The sheath 312 also has a non-circular cross section, both internally and externally. The internal cross section is configured to fit closely about the exterior of the base or pin portion 214 of the analog and pin 212 in order to prevent the analog and pin 212 from rotating within the sheath 312, while the non-circular exterior of the sheath 312 prevents it from rotating when installed in the stone model (analog of the oral structure of the patient) for the manufacture of the dental prosthesis. Additional anti-rotation means may be provided by one or more circumferentially discontinuous bands or rings 340 disposed about the sheath 312. The bands 340 may have breaks or discontinuities 342 therein to preclude rotation of the sheath 312 within the stone die or model.

The analog and pin 212 is retained within the sheath 312 by a distal protruding tab 220 that extends from the tip of the pin portion 214 and through a hole 320 in the tip of the sheath 312. The base or pin portion 214 of the analog and pin 212 is installed in the sheath 312 with the tab 220 protruding through the hole 320 in the base of the sheath, and a washer 366 is placed over the tab 220. The tab 220 includes a passage 222 therethrough, through which a retaining pin 322 is placed to secure the analog pin 212 within the sheath 312 for the duration of manufacture of the dental prosthesis, e.g., single tooth prosthesis P3; multiple units would be required for a denture having multiple teeth.

A lab processing coping 150 is provided for the manufacture and permanent installation of the dental prosthesis P3 thereon. The lab processing coping 150 is formed as a thin shell and includes an internal cavity or recess 158a closely matching and mating with the contours and shape of the abutment 216 of the analog pin 212. The internal cavity or recess 158a is devoid of any rings or other retaining structure, as it must be removable from the abutment analog 216 of the analog and pin 212. The external shape and contour 158b closely matches the internal shape and contour of the receptacle 136 of the transfer coping 134. This permits the dental prosthesis P3 to be manufactured on the lab processing (fixed) coping 150 with the coping 150 installed securely on the abutment analog portion 216 of the analog and pin 212.

The prosthesis manufacturing process initially involves the installation of the lab processing coping 150 on the abutment analog portion 216 of the analog and pin 212, once the transfer coping 134 and its impression I (FIG. 4) have been removed. A handling tab 152 extends from the tip of the lab processing coping 150, allowing the dentist to handle the coping during intraoral procedures. The dental prosthesis P3, e.g., a single prosthetic tooth, is then constructed on the lab processing coping 150. When this has been accomplished, the stone model with the analog and pin 212, coping 150, and completed dental prosthesis P3 are returned to the dentist for installation on the abutment 116 of the insert 112 (FIG. 4) previously installed in the mouth of the patient.

FIG. 6 of the drawings provides an illustration of the completed placement of the fixed dental prosthesis P3. The implant 112 was previously installed in the mouth of the patient, with the abutment portion 116 extending above the gingival layer G. It will be noted that the sub-gingival flange 124, i.e., the "finish line" of the implant 112, is slightly below the surface of the gingival layer. This results in the lower, outer flange of the permanent coping 150 residing slightly below the gingival surface, with the lowermost edge of the prosthesis P3 also residing slightly below the gingival surface due to its congruency with the lower and outer flange of the coping 150. The result is much like a natural tooth; there is no gap between the gingival tissue and the structure of the prosthetic tooth P3.

Figure 7:
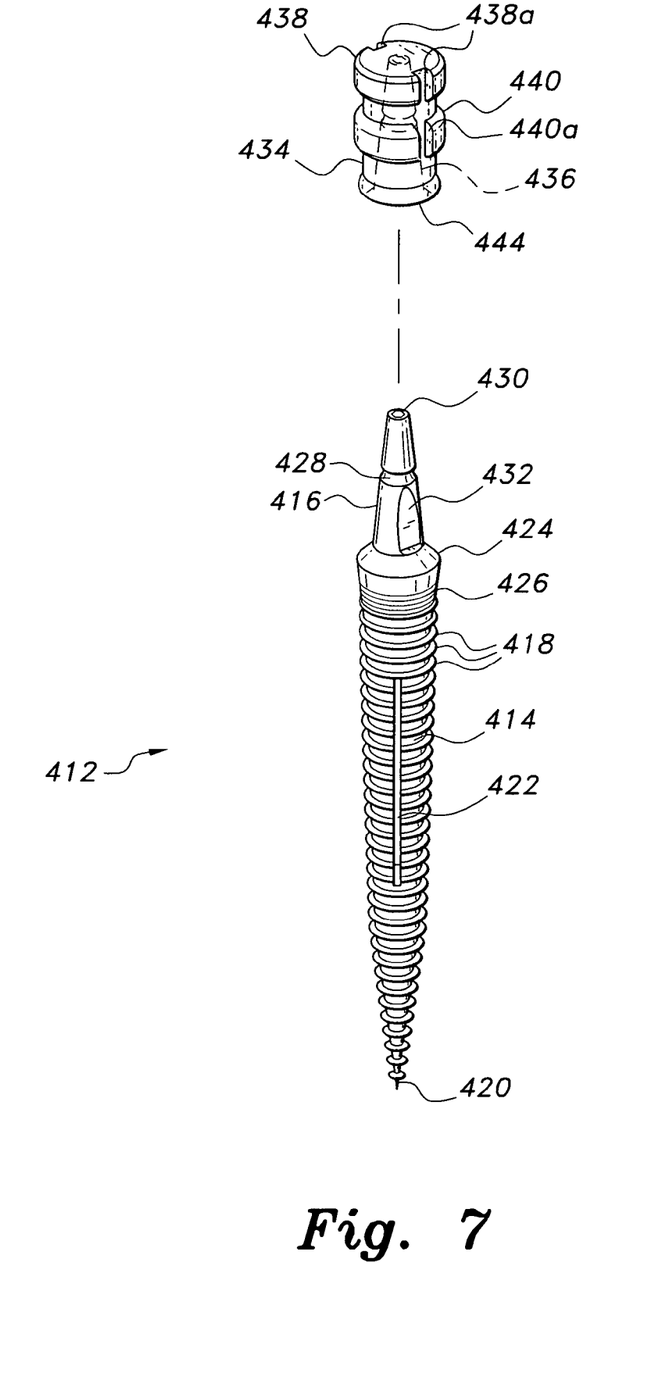
FIG. 7 is an exploded perspective view of an alternative embodiment of an implant and abutment in a dental implant system according to the present invention, shown with a corresponding transfer coping.
Figure 8:
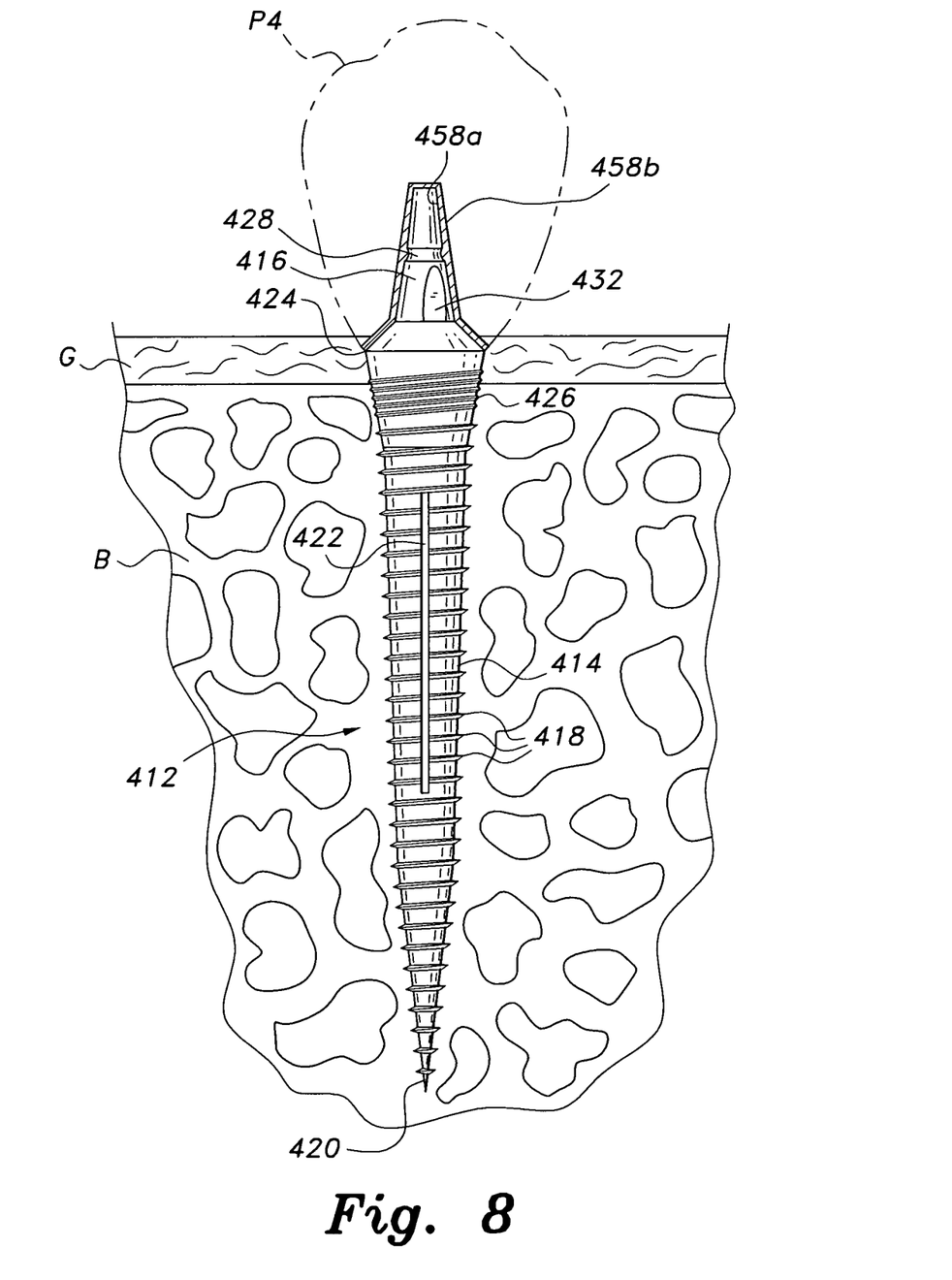
FIG. 8 is an elevation view in section of an installed implant in a dental implant system according to the present invention, shown with its coping and dental prosthesis affixed thereto.

FIG. 7 illustrates an implant 412 and transfer coping 434 for use therewith, with FIG. 8 illustrating the installed implant 412, and a lab processing coping 450 and dental prosthesis P4 cemented or otherwise fixed thereon. The implant 412 of FIGS. 7 and 8 is similar to the implant 112 of FIGS. 4 and 6, and is in fact identical thereto from the sub-gingival collar finish line 424 down, having a base 414 with helical threads 418 thereon and micro-threads 426 about the lower portion of the conical sub-gingival collar 424, a sharply pointed distal tip 420, and one or more axial grooves 422 formed along the base 414.

The abutment portion 416 of the implant 412 has a somewhat different configuration from the corresponding abutment 116 of the implant 112 of FIGS. 4 and 6, however. The abutment 116 is shaped for use with a forwardly positioned or anterior prosthetic tooth, e.g., an incisor, with such teeth having a somewhat thinner section in the fore-aft orientation. Thus, the non-circular, flattened shape of the abutment 116 also provides for the placement of a corresponding instrument thereon to rotate and thread the insert base 114 into the bone structure. However, the abutment 416 is intended for a more distal or posterior, i.e., rearward installation in the mouth to support a molar-type tooth having a more uniform width or thickness in both longitudinal and lateral orientations. Accordingly, the abutment 416 has a more conical shape with a truncated top, with the circumferential groove 428 being located closer to the midpoint of the conical portion. A flat 432 is formed in the conical surface of the abutment 416, providing a non-circular cross section at that point for an instrument to grip the abutment 416 (and thus the base portion 414 of the implant 412, formed integrally therewith), for applying torque to advance the implant 412 through the soft tissue and into the underlying bone. Alternatively, a tool or instrument bit receptacle 430 having a non-circular cross section may be provided in the upper end of the abutment 416 (or the abutments of other implants disclosed herein), if so desired.

The transfer coping 434 of FIG. 7 includes an abutment receptacle 436 defined therein that is configured to fit closely about the abutment 416 and thus the analog of the abutment. The transfer coping 434 has an external shape essentially identical to that of the transfer coping 134 of FIG. 4, i.e., a generally cylindrical external shape, with an outwardly extending circumferential flange 438 about the head or upper end thereof and an outwardly protruding circumferential band 440 extending about the coping 434. The flange 438 and/or band 440 are preferably non-circular, i.e., having a flat or other non-circular discontinuity formed thereon or therein in the manner of the flat 32 formed along the side or edge of the head 30 of the abutment 16 of FIG. 1. This prevents the impression (e.g., similar to the impression I shown in broken lines in FIG. 4) from rotating thereon. A discontinuity or gap, respectively 438a and 440a for the flange 438 and band 440, may be provided to serve this function. An outwardly extending or flaring skirt or flange 444 extends circumferentially about the base of the transfer coping 434 from the "finish line," i.e., the juncture between the base of the cylindrical body of the coping 434 and the skirt or flange 444. This skirt or flange 444 serves to expand and hold back the gingival tissue during the fitting of the transfer coping 434 during the making of the impression, in a manner similar to the use of packing cord about a natural tooth that has been prepared for a fixed prosthetic restoration.

The process of forming and installing a single, fixed prosthetic tooth, e.g., the prosthetic tooth P4 of FIG. 8, is essentially the same as that described further above for the components illustrated in FIGS. 4 through 6. The end result is generally as illustrated in FIG. 8 of the drawings. The lab processing or fixed coping 450 is installed upon the abutment 416, and the dental prosthesis P4 is affixed upon the coping 450, and thus upon the abutment 416 of the previously installed implant 412. The lab processing coping 450 is formed in a manner similar to the coping 150 of FIGS. 5 and 6, i.e., as a thin shell including an internal cavity or recess 458a closely matching and mating with the contours and shape of the abutment 416 of the implant 412. The external shape and contour 458b has a similar shape and configuration, with the prosthetic tooth P4 being formed thereover. As in the case of the installation illustrated in FIG. 6, the sub-gingival collar 424 is slightly below the surface of the gingival layer. This results in the finish line of the fixed coping 450 residing slightly below the gingival surface, the lowermost edge of the prosthesis P4 also residing slightly below the gingival surface due to its congruency with the lower and outer flange of the coping 450. The result is much like a natural tooth, with no gap between the gingival tissue and the structure of the prosthetic tooth P4.

In the case of the removable prostheses shown in FIGS. 1 and 2, the dental implant system allows the prostheses to be installed and removed quickly and easily by the user thereof, while still providing secure retention in the mouth. The resilient components used in the system may be quickly and easily replaced as needed. In the case of the fixed prostheses of FIGS. 6 and 8, the durability and security of the installation should provide years of use for the user, and could last for the life of the user. In either case, the relative simplicity of installation provides many benefits both to the dental practitioner and to the patient, with those benefits providing more rapid and thus less costly installation.

It is to be understood that the present invention is not limited to the embodiments described above, but encompasses any and all embodiments within the scope of the following claims.

I claim:

1. A kit for a dental prosthesis, comprising:
   a dental prosthesis having at least one prosthesis-retaining housing installed therein, wherein the housing is configured as a retaining cap and includes a circumferential flange at the upper, closed end and at least one inwardly extending flange at the lower, open end;
   a rubber insert removably installed within the housing, the insert having an abutment receptacle formed therein, the rubber insert including at least one slot formed about its periphery and configured to engage the lower end flange of the housing;
   at least one implant having an abutment formed integrally therewith, the implant including a tapered, helically threaded base portion having a pointed distal tip, a collar opposite the tip, the abutment extending from the collar, a micro-threaded portion disposed between the collar and the base portion, and a head disposed upon the abutment opposite the collar, the head being the terminal portion of the abutment and having a non-circular periphery, the implant being adapted for implanting in a patient's mouth, the prosthesis being retained in the patient's mouth when the abutment receptacle is seated on the abutment; and a ring having a central passage therein to fit about the abutment.

2. The kit for a dental prosthesis according to claim 1, wherein the dental prosthesis is selected from the group consisting of removable partial dental prostheses and removable full dental prostheses.

3. The kit for a dental prosthesis according to claim 1, wherein the dental prosthesis is a single fixed prosthetic tooth.

4. The kit for a dental prosthesis according to claim 1, wherein:
   the housing has an inwardly disposed base flange, the base flange having a plurality of radially disposed slots therein; and
   the insert has a plurality of axial ribs extending radially therefrom, the ribs being removably insertable through the slots of the base flange of the housing, the ribs being captured by the base flange when the insert is rotated in the housing in order to secure the insert in the housing.

5. The kit for a dental prosthesis according to claim 4, further comprising an insert installation and removal instrument having an elongated shaft and a bit attached to an end of the shaft, the abutment receptacle having a slot defined therein for receiving the bit.

6. A dental implant assembly for engaging a prosthesis, comprising:
   a housing, the housing being configured as a retaining cap and including a circumferential flange at the upper, closed end and at least one inwardly extending flange at the lower, open end;
   an insert installed within the housing, the insert having a top surface, a bottom surface and an abutment receptacle formed therein, the insert including at least one slot formed about its periphery and configured to engage the lower end flange of the housing; and
   an implant having an abutment formed integrally therewith and being configured for engagement with the abutment receptacle in the insert, the implant including a tapered, helically threaded base portion having a pointed distal tip, a collar opposite the tip, the abutment extending from the collar, a micro-threaded portion disposed between the collar and the base portion, and a head disposed upon the abutment opposite the collar, the head being the terminal portion of the abutment and having a non-circular periphery, the implant being adapted for implanting in a patient's mouth; and a ring having a central passage therein to fit about the abutment.

7. A dental implant assembly according to claim 6, wherein the insert is rubber.

8. A dental implant assembly according to claim 6, wherein the ring is elastomeric.

9. A dental implant assembly according to claim 6, wherein the ring is configured to abut the bottom surface of the insert.

10. A dental implant assembly according to claim 6, wherein:
    the housing has an inwardly disposed base flange, the base flange having a plurality of radially disposed slots therein; and
    the insert has a plurality of axial ribs extending radially therefrom, the ribs being removably insertable through the slots of the base flange of the housing, the ribs being captured by the base flange when the insert is rotated in the housing in order to secure the insert in the housing.

11. The kit for a dental prosthesis according to claim 1, further including a ring, the ring having a central passage therein to fit about the abutment.

12. A dental implant assembly for engaging a prosthesis, comprising:
    a housing, the housing being configured as a retaining cap having a continuous, imperforate outer surface and including a circumferential flange at the upper, closed end and at least one inwardly extending flange at the lower, open end;
    an insert readily removably installed within the housing, the insert having a top surface, a bottom surface and an abutment receptacle formed therein, the insert including at least one slot formed about its periphery and configured to engage the lower end of the inwardly extending flange of the housing; and
    an implant having an abutment formed integrally therewith and being configured for ready removable engagement with the abutment receptacle in the insert, the implant including a tapered, helically threaded base portion having a pointed distal tip, a collar opposite the tip, the abutment extending from the collar, and a head disposed upon the abutment opposite the collar, the head being the terminal portion of the abutment and having a non-circular periphery, the implant being adapted for implanting in a patient's mouth; and a ring having a central passage therein to fit about the abutment.

* * * * *